(12) United States Patent
Donati

(10) Patent No.: US 8,709,826 B2
(45) Date of Patent: Apr. 29, 2014

(54) ANALYTE ASSAYING BY MEANS OF IMMUNOCHROMATOGRAPHY WITH LATERAL MIGRATION

(75) Inventor: Raphael Donati, Radon (FR)

(73) Assignee: Vedalab, Alencon (FR)

( * ) Notice: Subject to any disclaimer, the term of this patent is extended or adjusted under 35 U.S.C. 154(b) by 890 days.

(21) Appl. No.: 11/990,923

(22) PCT Filed: Aug. 23, 2006

(86) PCT No.: PCT/IB2006/002308
§ 371 (c)(1),
(2), (4) Date: Mar. 6, 2009

(87) PCT Pub. No.: WO2007/023372
PCT Pub. Date: Mar. 1, 2007

(65) Prior Publication Data
US 2009/0280576 A1 Nov. 12, 2009

(30) Foreign Application Priority Data
Aug. 23, 2005 (FR) ..................................... 05 08685

(51) Int. Cl.
*G01N 33/558* (2006.01)

(52) U.S. Cl.
USPC ........... 436/514; 436/164; 436/169; 436/172; 436/807; 436/518; 435/7.1; 435/283.1; 435/287.1; 435/287.2; 435/287.7

(58) Field of Classification Search
USPC ......... 436/164, 169, 172, 807, 518, 514, 528; 435/7.1, 283.1, 287.1, 287.2, 287.7
See application file for complete search history.

(56) References Cited

U.S. PATENT DOCUMENTS

| | | |
|---|---|---|
| 5,962,339 A | 10/1999 | Midgely |
| 6,664,114 B1 | 12/2003 | Lackie et al. |
| 2001/0004532 A1* | 6/2001 | Chandler ........................ 436/530 |
| 2002/0146754 A1* | 10/2002 | Kitawaki et al. .............. 435/7.93 |

(Continued)

FOREIGN PATENT DOCUMENTS

| | | |
|---|---|---|
| DE | 100 54 093 A1 | 5/2002 |
| EP | 0 291 194 B2 | 2/1994 |

(Continued)

OTHER PUBLICATIONS

Hansen, "Fluorescent dextran conjugates for use in quantitative assays," *IVD Technology*, vol. 4, pp. 35-40 (2003).

(Continued)

*Primary Examiner* — Melanie Y Brown
(74) *Attorney, Agent, or Firm* — Oliff PLC

(57) ABSTRACT

The invention relates to a device for determining an analyte in a liquid sample. The inventive device consists of: a capillary action means, involving lateral migration, defining a reference capillary action direction and comprising a liquid sample deposit area and an analytedetection area which is disposed downstream of the deposit area; a first analytespecific binding reagent which is conjugated to a visible and/or measurable marker and which is free to migrate when wet by means of capillary action in the abovementioned capillary actions means along the reference direction; and a second analytespecific binding reagent which is immobilized in the detection area. The invention is characterized in that the detection area comprises the analyte or an analogue of the analyte, which is immobilized and disposed at a distance from the second specific binding reagent.

18 Claims, 2 Drawing Sheets

(56) References Cited

U.S. PATENT DOCUMENTS

Figure 1:
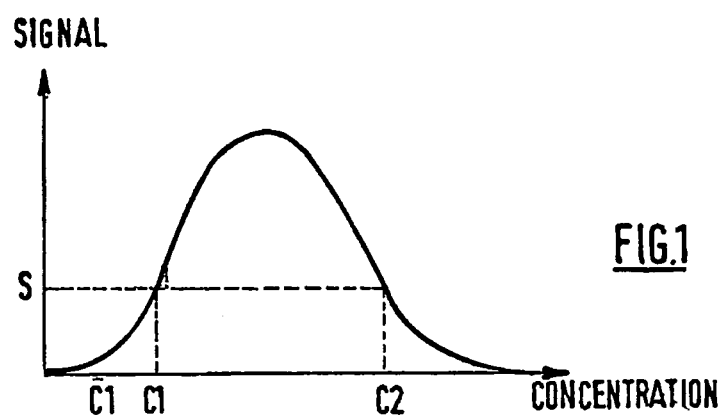

| | | | |
|---|---|---|---|
| 2002/0146844 A1* | 10/2002 | Pronovost et al. | 436/514 |
| 2003/0113713 A1* | 6/2003 | Glezer et al. | 435/5 |
| 2005/0112779 A1 | 5/2005 | Wei et al. | |
| 2006/0134802 A1 | 6/2006 | Donati et al. | |

FOREIGN PATENT DOCUMENTS

| | | |
|---|---|---|
| EP | 0 284 232 B2 | 6/1995 |
| EP | 0 560 411 B1 | 7/2000 |
| EP | 0 560 410 B1 | 10/2002 |
| EP | 1 091 808 B1 | 7/2003 |
| JP | A-2002-122599 | 4/2002 |
| JP | A-2004-085425 | 3/2004 |
| WO | WO 00/00288 A1 | 1/2000 |
| WO | WO 2004/088320 A1 | 10/2004 |

OTHER PUBLICATIONS

English-language Translation of Apr. 19, 2011 Japanese Office Action issued in JP-2008-527534.

\* cited by examiner

SAMPLE WELL    READING WINDOW

SAMPLE BUFFER    CONJUGATED    hCG    GOAT ANTI-MOUSE ANTIBODY    ABSORBENT BUFFER

ANTI-HCG POLYCLONAL ANTIBODIES
CAPILLARY ACTION DIRECTION

ANALYTE ASSAYING BY MEANS OF IMMUNOCHROMATOGRAPHY WITH LATERAL MIGRATION

The present invention relates to an immunochromatography device with lateral migration enabling simultaneous determination of an analyte in a liquid sample using a sandwich test and using a competition test.

Immunochromatographic devices with lateral migration are described, for example, in patent EP 0 284 232. These devices implement a capillary action means in the form of a porous solid support within which the sample and reagents migrate by capillary action. These devices thus integrate or comprise a porous solid (or immunochromatographic) support comprising a first supporting area in lyophilized, dry or dehydrated form, an analyte-specific binding reagent conjugated to a visible and/or measurable marker, and a detection area whereon is immobilized an analyte-specific capture reagent. The analyte-specific binding reagent is immobile when dry, but becomes mobile in the solid support when wet. Thus, when the solid support is put in contact with a liquid sample, the latter migrates by capillary action in this support, driving the analyte-specific binding reagent conjugated to the visible and/or measurable marker. The sample and the analyte-specific binding reagent migrate by capillary action in the solid support to the detection area bearing the immobilized analyte-specific capture reagent.

One knows from WO 2004/088320 immunochromatographic methods in solid phase in which the binding reagent, conjugated to a visible and/or measurable marker, is extemporaneously added in liquid form.

These devices traditionally enable detection of the analyte, either by a sandwich test or a competition test.

In a sandwich test, the marked binding reagent binds to the analyte, and the latter is immobilized on the solid support by the capture reagent. The presence or absence of the analyte in the sample is measured by the presence or absence of a visible or measurable signal, at the level of the capture reagent.

In a competition test, the analyte and the binding reagent are in competition to bind to the capture reagent. The presence or absence of the analyte in the sample is measured by the absence or presence of a visible or measurable signal, at the level of the capture reagent.

Patents EP 0 291 194, EP 0 560 411 and EP 0 560 410 describe devices wherein the immunochromatographic solid support in only one part is incorporated into a case provided with an opening for depositing of the liquid sample, and an observation window to read the result.

Patent EP 1 091 808 describes improved devices also comprising a porous solid support in several parts, with a capture member for the liquid sample, mobile, allowing better collection of the sample.

These devices can be adapted for a single and at-home usage. Indeed, they are easy and quick to use, requiring very little manipulation since all of the reagents are integrated or comprised in the device.

However, these immunochromatographic tests in solid phase do not make it possible to determine the quantity of the analyte in the sample.

Moreover, in the sandwich test, for some analytes a "hook" effect has been observed. The hook effect is a well-known undesirable effect in immunological tests. It occurs when the analyte is present in the sample at a very high concentration. The hook effect can then lead to false negatives, erroneously concluding the absence of the analyte in the sample.

The analytes which present a hook effect during sandwich-type immunological assays have signal/concentration curves of the Gauss curve type (see FIG. 1). FIG. 1 shows that to a given signal (S) correspond two possible concentrations of the analyte (C1 and C2), one weak (C1) and the other strong (C2) during reading of the result at a defined time.

Figure 2:
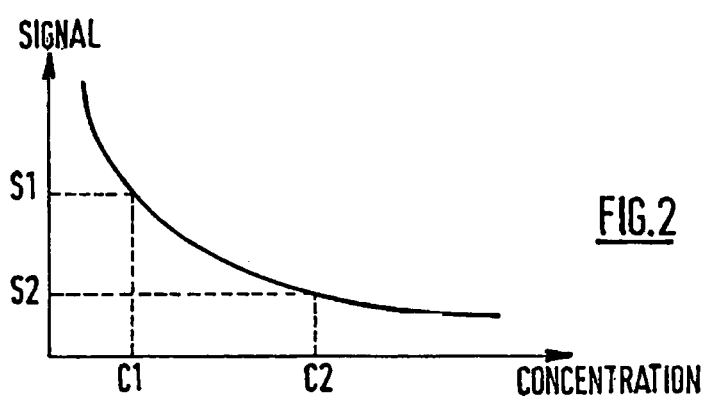

The signal/concentration curves for assays using competition are shown in FIG. 2. For a competition test, two different signals (S1 and S2) are obtained for two different respective concentrations (C1 and C2) of the analyte to be assayed.

However, competition tests also reveal their limitations very quickly, as the signal becomes extinct at relatively low concentrations of the analyte.

One solution commonly adopted to resolve these drawbacks of sandwich and competition tests consists of assaying the analyte, from a dilution series of the liquid sample. The use of a dilution series is not, however, appropriate for at-home usage. Moreover, usage of a dilution series of the sample requires additional manipulation and increased consumption of single-use test devices, since each sample is tested several times at different dilutions.

According to document DE 10054093, one proposes an immuno-filtering device made up of two distinct or independent parts, assigned to a sandwich-type test and a competition-type test, respectively. With this device, a specific binding reagent conjugated to a fluorescent marker is extemporaneously mixed with the analyte. The mixture obtained is then divided into two portions. A first portion is filtered in the sandwich part, and reacts with a second binding reagent, immobilized, and a second portion is filtered in the competition part of the device, and reacts with a capture reagent which is immobilized and identical to the analyte, or an analogue of the analyte. The fluorescent signals respectively obtained make it possible to determine the analyte.

This device is not of a nature to improve the sensitivity or precision of determination of the analyte, as each elementary test works with the initial concentration of the specific binding reagent.

According to document US 2005/0112729 (cf. in particular paragraph 0063 and claim 1), one describes a device for determining a complex between an analyte and a first specific binding reagent which is marked, this device comprising:
  a capillary action means,
  in one so-called competition area of the capillary action means, a second analyte-specific binding reagent, which is immobilized and complexed with a ligand, also marked,
  a so-called detection area of the capillary action means, a capture reagent which is immobilized and able to bind itself both to the aforementioned complex and the marked ligand, the latter being able to be displaced or decomplexed in the competition area by the circulation of said complex on the capillary action means.

Determination of the analyte is obtained from signals obtained in the competition and detection areas.

The format of this test is complex to implement, and is justified only for high-precision determination of the analyte.

The present invention aims to resolve the drawbacks of the previously discussed devices. In particular, the present invention relates first to a test device, and also to a usage method of the latter, allowing determination of the analyte, with a sufficient degree of reliability and/or precision, in all circumstances, i.e. regardless of the initial concentration of said analyte, in particular when this concentration is relatively strong or relatively weak.

Figure 3:
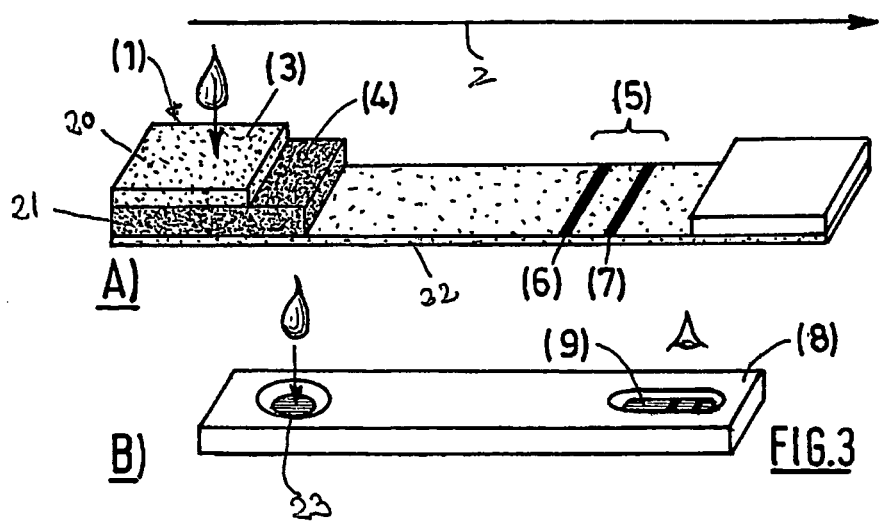

According to the invention, in reference to FIG. 3, one proposes a device for determining an analyte in a liquid sample, comprising:

a capillary action means 1, involving lateral migration determining a reference capillary action direction 2, comprising a liquid sample deposit area 3, and an analyte detection area 5 which is disposed downstream of said deposit area, a first analyte-specific binding reagent 4, conjugated to a visible and/or measurable marker, and which is free to migrate when wet by means of capillary action, in the above-mentioned capillary action means 1, along the reference direction, a second analyte-specific binding reagent 6 which is immobilized in the detection area 5, characterized in that the detection area 5 comprises the analyte, or an analogue of the analyte, which is immobilized and disposed at a distance from the second specific binding reagent 6.

This device preferably has one or several of the following secondary characteristics, considered alone or in combination, still explained in reference to FIG. 3:

this device may comprise a liquid sample capture member, independent of the capillary action means, able to be brought into contact with the deposit area, for circulation of said sample into said deposit area.

the capillary action means 1 may comprise an area for disposing the first binding reagent 4, in the dry and free state, in or on said capillary action means; the area for disposing the first binding reagent is merged with the deposit area of the sample, or is disposed downstream of the latter, but upstream of the detection area 5.

in the detection area 5, the analyte 7, or the analogue of the analyte, is disposed upstream or downstream of the second specific binding reagent.

the second specific binding reagent 6, and/or the analyte 7, or the analogue of the analyte, are disposed for example on the capillary action means along a line transverse to the reference direction.

the capillary action means can comprise a control area (C), downstream of the detection area 5.

According to the present invention, the term "capillary action means" refers to any means constituting or acting as a continuous capillary action unit, by lateral migration (i.e. which is perpendicular to the thickness of the capillary material(s) implemented for capillary action). One such capillary action means is, for example, an oblong support along the direction and/or path of the capillary action (lateral migration), made up of a single and same capillary or porous material, or by several different capillary elements or materials, arranged in relation to each other, for example overlapping, to obtain a continuity of capillary circulation from one element or material to another, along the direction of capillary action.

A capillary action means of this type determines a direction and/or path of capillary action for all liquid which is received or deposited at one end, toward the other end of said means.

The capillary, or immunochromatographic by lateral migration, action considered according to the present invention must be distinguished from that implemented in immuno-filtering techniques, according to which the liquids permeate the thickness of the porous filtration materials.

According to the present invention, the analyte, or the analogue of the analyte being considered, forms the third reagent, in addition to the first and second binding reagents. This third reagent is fixed or immobilized in the detection area, using any suitable means. This third reagent on the capillary action means is available to react specifically with the first specific binding reagent, to the exclusion of all other entities. In particular, once deposited on the capillary action means, it is not complexed with any other entity, or reagent, for example conjugated to a visible and/or measurable marker.

A device of this type may be implemented according to the method or usage form defined below, in reference to FIG. 3:

the liquid sample is deposited in the deposit area of the capillary action means, a sufficient time is allowed to pass for the migration by capillary action of the liquid sample to the detection area 5, one observes, in the detection area, the extent to which, on one hand the specific binding reagent 4 complexed with the analyte attaches itself to the second specific binding reagent 6, obtaining a first signal, and on the other hand the first non-complexed binding reagent attaches itself to the analyte 7, or the analogue of the analyte, obtaining a second signal, the analyte is determined from the first and second signals.

Preferably, according to the invention, the quantity of the first binding reagent 4 is greater than the quantity of the analyte present in the liquid sample, or the number of complexing sites with the first binding reagent, present in said liquid sample.

In a qualitative mode, a weak analyte concentration is detected by the absence of the first signal and the presence of the second signal; and a significant analyte concentration is detected by the absence of both signals. A normal analyte concentration is detected by the presence of the first and second signals.

Advantageously, the devices and/or methods according to the present invention make it possible to assay analytes weakly or very strongly concentrated in a sample without obtaining false positive or false negative results. Moreover, surprisingly, the devices and/or methods according to the present invention allow quantitative assaying of the analyte.

The devices and/or methods according to the invention are particularly well-suited to assaying of analytes presenting a significant hook effect such as the pregnancy hormone (hCG), C-reactive protein, albumin, etc.

DESCRIPTION OF THE INVENTION

The present invention therefore relates to a device for determining an analyte in a liquid sample, comprising a capillary action means (1) comprising, in the direction of capillary action (2):

a) a sample deposit or reception area (3);
b) an analyte-specific binding reagent conjugated to a visible and/or measurable marker, and which is free to migrate by capillary action when wet in the capillary action means (1);
c) an analyte-detection area (5);

wherein the analyte detection area (5) comprises, successively, in the direction of capillary action (2), on one hand a second, immobilized analyte-specific binding reagent (6), and on the other hand the immobilized analyte (7), or an analogue of the analyte; such that the first analyte-specific binding reagent (4) and the second analyte-specific binding reagent (6) make it possible to determine the analyte in the liquid sample by a sandwich test, whereas the first analyte-specific binding reagent (4) and the immobilized analyte (7), or analogue of the analyte, allow determination of the analyte in the liquid sample using a competition test.

In one embodiment, the first analyte-specific binding reagent (4), conjugated to a visible and/or measurable marker, is deposited dry on the support, and the invention therefore relates to a device for determining an analyte in a liquid sample comprising a capillary action means (1) comprising, in the direction of capillary action (2):

a) a sample deposit area (3);

b) a first analyte-specific binding reagent (4), conjugated to a visible and/or measurable marker, deposited dry and free to migrate when wet in the capillary action means (1);

c) an analyte-detection area (5);

wherein the analyte-detection area (5) comprises, successively, in the direction of capillary action (2), a second analyte-specific binding reagent (6), immobilized, and the analyte (7), or an analogue of the analyte, immobilized; such that the first analyte-specific binding reagent (4) and the second analyte-specific binding reagent (6) enable determination of the analyte in the liquid sample by a sandwich test, while the first analyte-specific binding reagent (4) and the analyte (7), or the analogue of the analyte, immobilized, enable determination of the analyte in the liquid sample by a competition test.

In another embodiment, the first analyte-specific binding reagent (4), conjugated to a visible and/or measurable marker, is extemporaneously added in the form of a reagent in liquid form.

The term "reagent in liquid form" refers to any reagent in which the binding reagent is in a solution or suspension. Preparation of the binding reagent conjugated to the visible and/or measurable marker in liquid form is done according to the techniques described in the literature. Typically, the conjugated binding reagent is in a solution or suspension in a buffered saline solution. This solution may also include stabilizing agents and other compounds, for example anti-bacterial or antifungal. Such stabilizing agents include, for example, bovine albumin serum (BSA) and casein.

In some methods according to the present invention, a thinner is used when the liquid sample is plasma, serum or whole blood, for example. This thinner migrates in the solid support driving the sample, and the marked binding reagent. Typically, this thinner is made up of a buffered saline solution, and may also comprise a detergent or any other component necessary for the reaction.

Preferably, the first analyte-specific binding reagent (4) is conjugated to a specific marker.

Preferably, the capillary action means (1) is a chromatographic test strip fixed on a rigid support.

In one preferred embodiment, the capillary action means (1) is integrated into a gripping support (8) provided with at least one observation window (9) making it possible to observe the detection area (5).

The term "binding reagent" refers to any chemical, biochemical or biological entity of a nature to bind specifically with the analyte, or with the capture reagent in competition with the analyte.

The terms "bind" and "binding" refer to any strong bond, for example covalent, or any weak bond, for example of the antigen/antibody or avidin/streptavidin type.

The binding reagent is, for example, an antibody, antigen or nucleic acid.

In a competition test, the binding reagent is in the solid phase and fixed to the analyte itself or a suitable analogue of the analyte. "Suitable analogue of the analyte" refers to any entity binding specifically to the first analyte-specific binding reagent, in competition with the analyte.

In a sandwich-type test, the first marked binding reagent is an anti-analyte conjugated to a visible and/or measurable marker, for example a specific antibody of the analyte, conjugated to said marker.

In a sandwich-type test, the second binding reagent binds specifically to the analyte. The second marked binding reagent is therefore also an anti-analyte, for example a specific antibody of the analyte conjugated to a visible and/or measurable marker.

The term "visible and/or measurable marker" refers to any marking method allowing direct or indirect detection by the naked eye, or with the help of an apparatus, due to the emission of a signal, said signal being, for example, a fluorescence, coloring, presence of an isotope, or a magnetic signal. For example, one can cite specially colored markers such as colloidal gold, or fluorescents, particles of colored latex, particles of fluorescent latex and particles conjugated to avidin and streptavidin.

The present invention therefore concerns a device for determining an analyte in a liquid sample, comprising a capillary action means (1), comprising, in the direction of capillary action (2):

a) a sample deposit or reception area (2);

b) a first specific antibody of the analyte (4), conjugated to a visible and/or measurable marker, and which is free to migrate by capillary action when wet in the capillary action means (1);

c) an analyte-detection area (5);

device wherein the analyte-detection area (5) comprises, successively, in the direction of capillary action (2), on one hand a second specific antibody of the analyte (6), immobilized, and on the other hand the analyte (7), or an analogue of the analyte, immobilized; such that the first analyte-specific antibody (4) and the second analyte-specific antibody (6) enable determination of the analyte in the liquid sample through a sandwich test, while, one on hand the first analyte-specific antibody (4), and on the other hand the analyte (7), or the analogue of the analyte, immobilized, enable determination of the analyte in the liquid sample through a competition test.

In one embodiment, the first analyte-specific antibody (4), conjugated to a visible and/or measurable marker, is deposited dry on the support, and the invention then concerns a device for determining an analyte in a liquid sample, comprising a capillary action means (1), and comprising, in the direction of capillary action (2):

a) a sample deposit or reception area (3);

b) a first analyte-specific antibody (4), conjugated to a visible and/or measurable marker, deposited dry and which is free to migrate through capillary action when wet in the capillary action means (1);

c) an analyte-detection area (5);

device wherein the analyte-detection area (5) comprises, successively, in the direction of capillary action (2), on one hand a second analyte-specific antibody (6), immobilized, and on the other hand the analyte (7), or an analogue of the analyte, immobilized; such that the first analyte-specific antibody (4) and the second analyte-specific antibody (6) enable determination of the analyte in the liquid sample through a sandwich test, while, on one hand the first analyte-specific antibody (4), and on the other hand the analyte (7), or the analogue of the analyte, immobilized, enable determination of the analyte in the liquid sample through a competition test.

In another embodiment, the first analyte-specific antibody (4), conjugated to a visible and/or measurable marker, is extemporaneously added in the form of a reagent in liquid form.

Preferably, the first analyte-specific antibody (4) is conjugated to a visible and/or measurable marker.

Preferably, the capillary action means (1) is a chromatographic test strip fixed on a rigid support.

In one preferred embodiment, the capillary action means (1) is integrated into a gripping support (8) provided with at least one observation window (9) making it possible to observe the detection area (5).

The invention also concerns a method for determining an analyte in a liquid sample, implementing a device as previously defined, comprising the following steps:

a) one has at least one capillary action means provided with at least one deposit or reception area, and a detection area, at least one capture reagent being immobilized in the detection area, b) one deposits, separately in the deposit area of the capillary action means, the liquid sample at least once, c) one waits a sufficient time for the migration through capillary action of the liquid sample to the area comprising the first specific binding reagent, conjugated to a visible and/or measurable marker, d) one waits a sufficient time for the migration through capillary action of the first specific binding reagent conjugated to a visible and/or measurable marker and of the liquid sample to the detection area, e) one observes the extent to which the specific binding reagent conjugated to a visible and/or measurable marker fixes itself in the detection area, to determine the analyte simultaneously through a sandwich test and a competition test.

According to one embodiment, the first specific binding reagent conjugated to a visible and/or measurable marker is deposited, dry and free, in or on the porous solid support.

According to one embodiment, the first specific binding reagent conjugated to a visible and/or measurable marker is extemporaneously added, in the form of a reagent in liquid form, simultaneously, after or before depositing of the analyte.

According to one embodiment, a thinner in liquid form is also added or deposited on the porous solid support.

According to one embodiment of the method, during step a), the detection area comprises at least two capture reagents, one of the two being the immobilized analyte or an analogue of the analyte, and the other of the two being an immobilized analyte-specific binding reagent.

The term "capture reagent" refers to any chemical, biochemical or biological entity of a nature to bind specifically with the analyte, or an analogue of the analyte.

In the case of a competition test, the capture reagent also binds to the first binding reagent. The analyte and the capture reagent typically form a ligand/anti-ligand, antigen/antibody, DNA/RNA or DNA/DNA pair. Thus, if the analyte is an antigen or a hapten, the capture reagent is, for example, a specific antibody of the analyte. If the analyte is an antibody, the capture reagent is the antigen recognized by the antibody or an antibody specifically recognizing the analyte. If the analyte is a nucleic acid, the capture reagent is for instance a complementary DNA probe.

The immobilized capture reagent is, for example, a polyclonal or monoclonal antibody having a strong affinity for the analyte, and more particularly it may be a monoclonal antibody.

To increase sensitivity, one may use, for example, an antibody marked according to techniques known by those skilled in the art for indirect detection, such as for example a biotinyl antibody, indirectly enabling detection through the formation of avidin-biotin and streptavidin-biotin entities.

These marked and biotinyl antibodies can also either be already directly deposited on a test-line, in the detection area, to increase sensitivity, or be deposited with the first specific antibody and be eluted and fixed such that the analyte and the antibody increase the contact time and again sensitivity in particular, for example, due to the number of fixing sites.

The analyte-specific capture reagent is immobilized on the solid support according to techniques known by those skilled in the art. This capture reagent is immobilized such that it is not mobile when wet. This immobilization can be done for example through absorption or by covalent coupling.

The term "anti-analyte" refers to any chemical, biochemical or biological entity of a nature to bind itself specifically with the analyte, or with the capture reagent, in competition with the analyte, for example an antibody, antigen or nucleic acid.

According to one embodiment, the invention also concerns a method for determining an analyte in a liquid sample, comprising the following steps:

a) one has a device as previously described;

b) one deposits a liquid sample in the deposit or reception area (3) of the capillary action means (1) of the device from step (a);

c) one waits a sufficient time for the migration by capillary action of the liquid sample from the deposit or reception area (3) to the detection area (5), driving the first analyte-specific antibody, conjugated to a visible and/or measurable marker (4);

d) one observes the extent to which the first analyte-specific antibody conjugated to a visible and/or measurable marker (4) is fixed in the detection area (5), to determine the analyte, simultaneously by a sandwich test and a competition test. In one advantageous embodiment, in step b) one deposits a liquid sample and a thinner in the deposit or reception area (3) of the capillary action means (1) of the device from step (a).

The term "analyte" refers to any chemical, biochemical or biological entity which one wishes to detect in a sample. Among the analytes detected by the devices and methods according to the present invention, are in particular proteins, peptides, antibodies, hormones, steroids, antigens derived from infectious agents or tumoral cells, infection agents such as bacteria, viruses or parasites, nucleic acids (DNA or RNA), therapeutic compounds, drugs or antibiotics.

The terms "detect" and "determine" refer to the determination of the presence or absence of an analyte in a sample, but also the measurement and quantification of an analyte in a sample. Indeed, the performances of the devices and methods according to the invention allow one to perform quantitative or semi-quantitative measurements.

In one particular embodiment of the invention, the analyte is hCG (choriogonadotropin hormone), C-reactive protein or albumin.

The term "liquid sample" refers to any sample wherein the analyte sought is in a solution or suspension. This liquid sample may in particular be any biological or bodily fluid. The liquid sample may also have been obtained directly or indirectly from a biological or bodily fluid. The sample can also be a liquid extract of a solid sample.

Typically, the liquid sample is urine, whole blood, plasma or serum.

In some methods according to the present invention, a thinner is used when the liquid sample is plasma, serum or whole blood for example. The thinner is deposited on the porous solid support with the sample. Alternatively, the thinner is deposited on the porous solid support before or after the sample. This thinner migrates in the solid support, driving, or facilitating the migration of the sample in the porous support, with the marked binding reagent. Typically this thinner is made up of a buffered saline solution; it may also comprise a detergent or any other component necessary for the reaction.

The term "capillary action means" refers to a porous solid support allowing the migration of a liquid by simple capillary action. The porosity of this support enables the capillary action (or lateral migration) of the liquid or wet sample and/or reagents. Such capillary action means are very widely used in all immunochromatography techniques with lateral migration, in particular.

Thus, the capillary action means implemented in the immunochromatographic devices according to the invention are well known by those skilled in the art (cf. EP 0 284 232). As an example, these capillary action means can be made up of various immunochromatographic supports, for example cellulose, nylon, nitrocellulose, polyethylene or glass fiber.

The capillary action means may be made up of one or several distinct parts. The various parts of the support can be made up of different materials. When the capillary action means is made up of different parts or different materials, these elements are disposed so as to enable continuity of capillary circulation in the capillary action means.

Typically, the capillary action means is made up of an oblong porous solid support along the direction of capillary action. Preferably, the capillary action means of the devices according to the invention comprises a porous solid support in the form of an immunochromatographic test strip. The capillary action means is present for example in the form of an immunochromatographic test strip made up of several superimposed or overlapping test strips.

The device according to the invention may, for example, be made up of a chromatographic test strip fixed on a rigid support. The rigid support may be made of various materials such as cardboard, plastic-coated cardboard or, most preferably, plastic materials. Preferably, the rigid support is made of polystyrene.

The capillary action means comprises a sample deposit or reception area, and a sample detection area. The deposit area and the detection area are distinct and separate from the capillary action means. These areas are disposed so as to allow the continuity of the capillary action from the deposit or reception area, to the detection area along a direction of capillary action. Typically, the deposit area and the detection area correspond respectively to the two opposite ends of the capillary action means. The capillary action means is thus, for example, made up of an oblong porous solid support along the direction of capillary action, having a proximal end and a distal end respectively forming the deposit area and the detection area.

These areas may, for example, be present on a same strip made of a single material. Advantageously, a specific porous material corresponds to each area of the capillary action means. A porous absorbent material can, for example, be used for the sample deposit area. Indeed, the deposit area of the capillary action means is intended to be put into contact with a flow of urine or to receive a liquid sample. One will therefore choose a suitable absorbent material. These materials are well known by those skilled in the art. And another absorbent material can be implemented for the area receiving the first specific binding reagent, and/or the detection area.

The sample deposit area of the capillary action means can cooperate with a capturing member in an absorbent material. This capture member can be put into direct contact with a flow of urine, for example. As described in WO 00/00288, the capture member can be mobile between two positions, one for collecting the liquid sample, at a distance from the capillary action means, and the other in continuity or capillary contact with the deposit area of the capillary action means.

The capillary action means bears, for example, a first analyte-specific antibody conjugated to a visible and/or measurable marker. This antibody is deposited dry in the capillary action means, and is free to migrate by capillary action when wet. This first analyte-specific antibody can be localized in the sample deposit or reception area. This first antibody can also, however, be deposited dry, downstream of the sample deposit or reception area, to avoid any loss of reagent through a washing effect upon depositing of the sample. Thus, the liquid sample is deposited in the deposit area of the capillary action means, then this sample migrates by capillary action through the capillary action means, then driving the first analyte-specific antibody conjugated to a marker.

Advantageously, the capillary action means can be incorporated into a gripping support. This gripping support facilitates manipulation of the capillary action means, and can also protect it, in particular from moisture.

The gripping support can partially or completely surround the capillary action means.

The gripping support can be formed from various materials such as cardboard, plastic-coated cardboard or, more preferably, plastic materials. Advantageously, the gripping support is made of a rigid and impermeable material. These gripping supports or cases are described in particular in patents EP 0 291 194, EP 0 560 411, EP 0 560 410 and EP 1 091 808.

The gripping support is usually in the form of a case.

In one embodiment of the invention, the capillary action means can comprise a sample deposit or collection area, protruding in relation to the gripping support, for receiving the liquid sample.

In another embodiment of the invention, the gripping support or the case comprises at least one opening for depositing the liquid sample.

Typically, the gripping support is also provided with at least one observation window to observe the detection area of the capillary action means.

The reagents implemented in the methods according to the present invention, enabling the determination of the analyte in the liquid sample, are well known by those skilled in the art.

The first analyte-specific antibody, conjugated to a visible and/or measurable marker, is deposited dry in or on the capillary action means, but it is free to migrate by capillary action when wet.

The second analyte-specific antibody is permanently immobilized in the detection area of the capillary action means.

The term "analyte-specific antibody" refers to an antibody capable of binding specifically with the analyte in an antigen/antibody type bond. It typically involves a polyclonal or monoclonal antibody having a strong affinity for the analyte. Preferably, it involves a monoclonal antibody.

The second analyte-specific antibody is immobilized in the detection area of the capillary action means according to techniques known by those skilled in the art.

This second antibody is immobilized such that it is not mobile when wet. This immobilization can be done for example by absorption or covalent coupling.

The first and second antibodies bind respectively and specifically with the analyte, for example on two epitopic sites, identical to or different from the analyte.

The first and second antibodies of the devices of the present invention enable determination of an analyte in the liquid sample through a sandwich test.

Moreover, the devices according to the present invention comprise the analyte itself, or an analogue of the analyte, immobilized in the detection area of the capillary action means.

The analyte, or the analogue of the analyte, is immobilized in the detection area of the capillary action area according to techniques known by those skilled in the art. The analyte, or the analogue of the analyte, is immobilized such that it is not mobile when wet. This immobilization can be done for example by absorption or by covalent coupling.

This second reagent of the detection area is identical to the analyte itself or a suitable analogue of the analyte. The term "suitable analogue of the analyte" refers to any entity binding itself specifically to the first binding reagent or specific antibody of the analyte, in competition with the analyte.

In one embodiment, on one hand, the first analyte-specific antibody, conjugated to a visible and/or measurable marker, and on the other hand the analyte, or the analogue of the analyte, immobilized in the detection area of the capillary action means, enable detection of the analyte of the liquid sample through a competition test. Preferably, the second analyte-specific antibody can be deposited upstream of the analyte, or of the analogue of the analyte, relative to the direction of capillary action.

The first analyte-specific antibody, which is free to migrate when wet, is conjugated to a visible and/or measurable marker, enabling measurement or direct observation of the result, of both the sandwich test and the competition test. Any visible marker can be observed directly by the naked eye when it is concentrated in the detection area of the capillary action means. Measuring the marker can be done directly by the naked eye, or with the help of a measuring device. This measurement is done by direct observation not requiring additional manipulation.

Advantageously, the devices according to the present invention comprise a first analyte-specific antibody conjugated to a visible and/or measurable marker.

The markers used according to the present invention enable direct detection by the naked eye, or indirect detection with the help of an apparatus, due to the emission of a signal, said signal being for example a fluorescence, coloring, present of isotope, magnetic signal.

One can cite, for example, particular makers, colored or fluorescent, made up of small particles insoluble in water and which therefore form suspensions, dispersions or sols, in liquid phase.

The particular markers are well known by those skilled in the art. Known in particular are colored or fluorescent particular markers, such as colloidal gold, particles of colored latex, fluorescent latex particles and particles conjugated to avidin or streptavidin, for example.

Among the markers enabling direct observation by the naked eye, we can also cite dextran-type markers (Hansen T. M., *IVD Technology* 4, 35-40, 2003). The binding reagent is then conjugated to a dextran chain (polysaccharide derivative) bearing fluorophores.

The binding reagents are conjugated to the visible and/or measurable marker according to techniques well known by those skilled in the art.

In one preferred embodiment of the invention, the detection area of the capillary action means comprises a third reagent arranged downstream of the second analyte-specific antibody, and downstream of the analyte, or of the analogue of the analyte, in relation to the direction of capillary action. This third reagent makes it possible to have a positive control so as to ensure effective capillary action of the liquid sample from the deposit area to the detection area of the capillary action means.

This third reagent is permanently immobilized in the detection area of the capillary action means.

It may involve, for example, an antibody binding itself to the first analyte-specific antibody conjugated to the marker. In this case, this third reagent makes it possible to verify migration of the first analyte-specific antibody conjugated to the marker, to the detection area of the capillary action means.

Alternatively, this third reagent is independent of the analyte and simply enables verification of the action of the liquid sample to the detection area.

The invention is described in more detail in reference to the following figures:

FIGURES

FIG. 1: Signal/concentration curve of the analyte for an immunological assay through a sandwich test FIG. 2: Signal/concentration curve of the analyte for an immunological assay through a competition test FIG. 3: Device for simultaneous assay of an analyte through a test according to the present invention FIG. 4: Rapid test device according to the present invention, comprising an immunochromatographic test strip in a case FIG. 5: Immunochromatographic test strip for hCG detection FIG. 6: Result of the test according to FIG. 5 in case of weak analyte concentration FIG. 7: Result of the test according to FIG. 5 in case of a strong analyte concentration FIG. 1 shows the signal/concentration curve obtained for an immunological assay through a sandwich test. The curve obtained is a curve of the Gauss curve type, which shows that to a given signal (S) correspond two possible concentrations of the analyte (C1 and C2), one weak (C1) and the other strong (C2) during reading of the result at a defined time.

FIG. 2 shows a signal/concentration curve for an assay through competition. One observes the obtaining of two different signals (S1 and S2) for two concentrations (C1 and C2) of the analyte to be assayed. However, one observes that the signal is extinct at relatively low concentrations of the analyte.

FIG. 3 shows a device for simultaneous assay of an analyte according to the present invention, the view A) presenting the device without gripping support and view B), the device comprising a gripping support.

View 3A shows the device comprising a capillary action means (1) comprising, in the direction of capillary action (2):

a) a deposit or reception area (3) of the sample on a first capillary material 20;

b) a first analyte-specific antibody (4), conjugated to a visible and/or measurable marker, which is free to migrate through capillary action when wet in the capillary action means (1); this first marked antibody is deposited, dry and free, on a second capillary material 21, in continual capillary circulation with the first capillary material 20;

c) an analyte-detection area (5) comprising successively, in the direction of capillary action (2), on one hand a second immobilized analyte-specific antibody (6), and on the other hand the analyte (7), or an analogue of the analyte, immobilized; the second antibody and the analyte (or the analogue of the analyte) are disposed or deposited on a third capillary material, in continual capillary circulation with the second capillary material 21;

View B) shows the capillary action means (1) integrated into a gripping support (8) provided with at least one observation window (9) making it possible to observe the detection area (5), and an opening 23 for collecting, depositing or receiving the liquid sample.

EXAMPLES

Pregnancy test (detection in urine of the choriogonadotropin hormone, or hCG)

Figure 4:
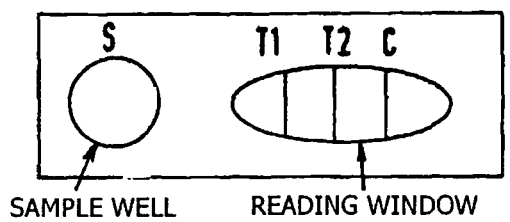
Figure 5:
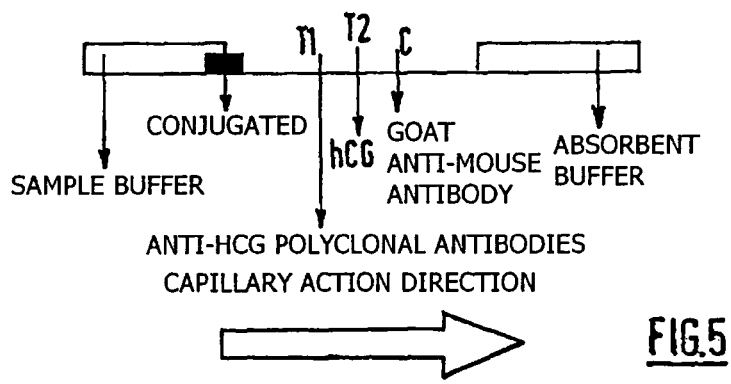

FIG. 4 shows an external view of a rapid test of the case type wherein is inserted a chromatographic test strip according to the present invention.

The test strip 1 contains an anti β-hCG monoclonal antibody 4 marked with colloidal gold, deposited on the glass fiber 21 and dehydrated (conjugated). This particular marker is dissolved by the liquid sample when it is deposited in the sample well (S), then successively comes into contact, through migration on the test strip, with a first area containing a fixed anti-hCG polyclonal antibody (T1), a second area containing fixed hCG (T2), and a third area containing a polyclonal goat anti-mouse immunoglobulin antibody (C), see FIG. 5.

Figure 6:
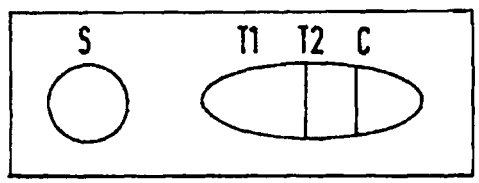

In case of absence (or very weak concentration) of the hCG hormone in the deposited sample, practically no visible reaction will occur in the area T1, while a line will appear in the area T2 and the area C (FIG. 6).

Figure 7:
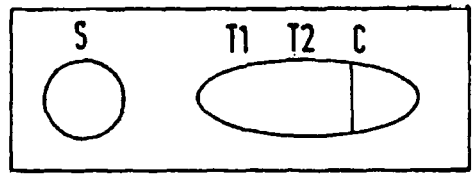

In case of a very strong hCG concentration in the sample, the reaction in the area T1 will be very weak or nonexistent (due to the "hook" effect previously described); no visible reaction will take place in the area T2, because nearly all of the anti β-hCG antibody marked with colloidal gold having reacted with the analyte (hCG) of the sample, is no longer available to react with the analyte (or any analogue of the analyte), and the area C will be positive (FIG. 7).

This system therefore makes it possible to effectively differentiate interpretation of the result in case of a low analyte concentration (2 positive lines: T2+C) or a strong analyte concentration (1 positive line: C). Moreover, the lines will appear in different places (T1 or T2).

The table below summarizes the results obtained in the detection area (T1, T2 and C) according to the analyte concentration in the sample with the help of a visual reading of the test.

TABLE 1

Results of visual reading of the test according to the hCG concentration in the sample.

| hCG Concentration (mIU/ml) | | | | | | | | |
|---|---|---|---|---|---|---|---|---|
| | 0 | 5 | 50 | 00 | .$10^3$ | .$10^4$ | $0^5$ | .$10^5$ |
| Line T1 | | /− | + | + | + | + | + | |
| Line T2 | + | + | + | + | + | + | + | |
| Line C | + | + | + | + | + | + | + | + |

In addition to a visual interpretation of the results, it is entirely possible to perform a reading using a machine, which is then able to provide a quantitative or semi-quantitative result of the analyte concentration, without prior dilution of the sample and without using concentration ranges. Indeed, depending on the concentration area, the results obtained in the detection area are different and the interpretation of this difference makes it possible, after calibration or by visual observation, to quantify the analyte concentrations.

The invention claimed is:

1. A device for determining an analyte in a liquid sample, comprising:
   a capillary action support, defining a reference capillary direction and comprising:
      a liquid sample deposit area; and
      an analyte-detection area disposed downstream of said deposit area, the analyte-detection area comprising a first detection area, and a second detection area disposed downstream of the first detection area;
      an area comprising a first analyte-specific binding reagent that is merged with the liquid sample deposit area, the first analyte-specific binding reagent being conjugated to a visible and/or measurable marker and being free to migrate when wet by means of capillary action in the capillary action support along the reference direction, and
      a second analyte-specific binding reagent immobilized in the first detection area,
   wherein:
      the analyte, or an analogue of the analyte, is directly fixed the capillary action support within the second detection area and disposed at a distance from the second specific binding reagent;
      the first detection area is configured to determine the analyte in the liquid sample by a sandwich assay;
      the second detection area is configured to determine the analyte in the liquid sample by a competition assay; and
      the device is configured to detect:
         a weak analyte concentration by the absence of a first signal in the first detection area and the presence of a second signal in the second detection area;
         a strong analyte concentration by the absence of the first and second signals in the first and second detection areas, respectively; and
         a normal analyte concentration by the presence of the first and second signals in the first and second detection areas, respectively.

2. The device according to claim 1, further comprising a liquid sample capture member, independent from the capillary action support, able to be brought into contact with the deposit area, for a flow of said sample in said deposit area.

3. The device according to claim 1, wherein the first specific binding reagent is in a dry state before use.

4. The device according to claim 1, wherein the second specific binding reagent, and/or the analyte, or the analogue of the analyte, are disposed on the capillary action support along a line transverse to the reference direction.

5. The device according to claim 1, further comprising a control area disposed downstream of the analyte-detection area, the control area comprising an area having a third reagent that is independent of the analyte.

6. The device according to claim 1, wherein the first analyte-specific binding reagent is present in excess of the analyte in the liquid sample.

7. The device according to claim 1, wherein the first analytes-pecific binding reagent is conjugated to a measurable marker and results of the device cannot be directly read by the naked eye.

8. The device according to claim 1, wherein the analyte, or the analogue of the analyte, is not conjugated to a visible and/or measurable marker.

9. The device according to claim 1, wherein the area comprising the first analyte-specific binding reagent is merged with the liquid sample deposit area such that the liquid sample deposit area is above the area comprising the first analyte-specific binding reagent.

10. The device according to claim 1, wherein the analyte is at least one selected from the group consisting of choriogonadotropin hormone (hCG), C-reactive protein and albumin.

11. The device according to claim 1, wherein the analyte is choriogonadotropin hormone (hCG).

12. A method for implementing a device according to claim 1, the method comprising:
   disposing the liquid sample in the deposit area of the capillary action support, waiting a sufficient time for the migration through capillary action of the liquid sample, detecting, in the first and second detection areas, the presence or absence of the first and second signals, determining whether the analyte is present from the first and second signals.

13. The method according to claim 12, wherein the quantity of the first binding reagent is greater than the quantity of the analyte present in the liquid sample, or the number of complexing sites present in said liquid sample.

14. The method according to claim 12, wherein a weak analyte concentration is detected by the absence of the first signal and the presence of the second signal.

15. The method according to claim 12, wherein a strong analyte concentration is detected by the absence of both signals.

16. A method for implementing a device according to claim 2, the method comprising:

disposing the liquid sample in the deposit area of the capillary action support, waiting a sufficient time for the migration through capillary action of the liquid sample, detecting, in the first and second detection areas, the presence or absence of the first and second signals, determining whether the analyte is present from the first and second signals.

17. A method for implementing a device according to claim 3, the method comprising:

disposing the liquid sample in the deposit area of the capillary action support, waiting a sufficient time for the migration through capillary action of the liquid sample, detecting, in the first and second detection areas, the presence or absence of the first and second signals, determining whether the analyte is present from the first and second signals.

18. A method for implementing a device according to claim 4, the method comprising:

disposing the liquid sample in the deposit area of the capillary action support, waiting a sufficient time for the migration through capillary action of the liquid sample, detecting, in the first and second detection areas, the presence or absence of the first and second signals, determining whether the analyte is present from the first and second signals.

* * * * *